(12) United States Patent
Müller et al.

(10) Patent No.: US 8,218,725 B2
(45) Date of Patent: Jul. 10, 2012

(54) METHOD AND DEVICE FOR ONLINE IMRT VERIFICATION

(75) Inventors: Lutz Müller, Nürnberg (DE); Caterina Brusasco, Bossiere (BE); Björn Hårdemark, Stockholm (SE); Johan Löf, Djursholm (SE); Anders Murman, Uppsala (SE)

(73) Assignees: Ion Beam Applications S.A., Louvain-la-Neuve; Raysearch Laboratories AB, Stockholm (SE)

( * ) Notice: Subject to any disclaimer, the term of this patent is extended or adjusted under 35 U.S.C. 154(b) by 370 days.

(21) Appl. No.: 12/513,143

(22) PCT Filed: Nov. 2, 2007

(86) PCT No.: PCT/EP2007/061836
§ 371 (c)(1),
(2), (4) Date: Mar. 8, 2010

(87) PCT Pub. No.: WO2008/053045
PCT Pub. Date: May 8, 2008

(65) Prior Publication Data
US 2010/0177872 A1      Jul. 15, 2010

(30) Foreign Application Priority Data
Nov. 3, 2006   (EP) .................................... 06123485

(51) Int. Cl.
*A61N 5/10* (2006.01)
*G01D 18/00* (2006.01)
(52) U.S. Cl. .......... 378/65; 378/207; 250/252.1
(58) Field of Classification Search ............ 378/65, 378/207; 250/252.1, 336.1, 370.07
See application file for complete search history.

(56) References Cited

U.S. PATENT DOCUMENTS
5,394,452 A     2/1995   Swerdloff et al.
(Continued)

FOREIGN PATENT DOCUMENTS
WO       03/092813 A1    11/2003

OTHER PUBLICATIONS

B. Poppe et al., "DAVID—a translucent muti-wire transmission ionization chamber for in vivo verification of IMRT and conformal irradiation techniques," Phys. Med. Biol. 51 (2006), 1237-1248.*

(Continued)

*Primary Examiner* — Allen C. Ho
(74) *Attorney, Agent, or Firm* — Fitch, Even, Tabin & Flannery, LLP

(57) ABSTRACT

A method is provided for monitoring and/or signalling errors of a radiation therapy apparatus during delivery of a radiation treatment to a target, the radiation therapy apparatus being configurable for a given radiation treatment by means of a beam shaping device. The method includes providing a radiation array detector between the beam shaping device and the target, capable of providing a measured detector response of the radiation treatment; determining a predicted detector response for successive times of the radiation treatment; measuring the measured detector response caused by the radiation beams for corresponding successive times of the radiation treatment; performing a comparison between the measured detector response and the corresponding predicted detector response; signalling in a short reaction time, an error when the comparison results in a difference which exceeds a given threshold. The disclosure also relates to a device comprising electronic 2-dimensional detectors, processor device and a main software.

12 Claims, 4 Drawing Sheets

U.S. PATENT DOCUMENTS

| | | | |
|---|---|---|---|
| 5,621,779 A * | 4/1997 | Hughes et al. | 378/65 |
| 5,754,622 A * | 5/1998 | Hughes | 378/65 |
| 6,038,284 A | 3/2000 | Hernandez-Guerra et al. | |
| 6,125,335 A * | 9/2000 | Simon et al. | 702/85 |
| 6,594,336 B2 * | 7/2003 | Nishizawa et al. | 378/65 |
| 6,810,107 B2 * | 10/2004 | Steinberg | 378/65 |
| 6,853,702 B2 | 2/2005 | Renner | |
| 2003/0174808 A1 | 9/2003 | Hughes et al. | |
| 2009/0200476 A1 * | 8/2009 | Brusasco et al. | 250/370.07 |
| 2010/0215147 A1 * | 8/2010 | Muller et al. | 378/65 |

OTHER PUBLICATIONS

R. Bonin et al., "A pixel chamber to monitor the beam performances in hadron therapy," Nuclear Instruments and Methods in Physics Research A 519 (2004) 674-686.*

J.M. Kapatoes et al., "Delivery Verification in Sequential and Helical Tomotherapy." Physics in Medical and Biology, (1999) vol. 44, pp. 1815-1841.

J.M. Kapatoes et al., "A Feasible Method for Clinical Delivery Verification and Dose Reconstruction in Tomotherapy." Medical Physics, Apr. 2001, vol. 28, Issue 4, pp. 528-542.

J.M. Kapatoes et al., "On the Accuracy and Effectiveness of Dose Reconstruction for Tomotherapy." Physics in Medical and Biology, (2001) vol. 46, pp. 943-966.

International Search Report, International Application No. PCT/EP2007/061787; date of completion Feb. 19, 2008, 4 pages.

International Search Report, International Application No. PCT/EP2007/061836; date of completion Mar. 20, 2008, 4 pages.

* cited by examiner

METHOD AND DEVICE FOR ONLINE IMRT VERIFICATION

CROSS REFERENCE TO RELATED APPLICATIONS

This application is a national phase application of International Application No. PCT/EP2007/061836, filed Nov. 2, 2007, claiming priority to European Patent Application No. 06123485.2, filed Nov. 3, 2006, which are incorporated by reference herein in their entireties.

FIELD OF THE INVENTION

The present invention relates to intensity modulated radio therapy (IMRT) used to deliver radiation doses. More particularly, the present invention relates to a method and a device for IMRT verification.

State of the Art

IMRT is a type of conformal radiation, which shapes radiation doses to closely approximate the shape of a tumour. More particularly, it is an advanced high-precision radiotherapy that utilizes computer-controlled x-ray or electron beams in order to deliver precise radiation doses to a malignant tumour or specific areas within the tumour. The radiation dose is designed to conform to the three-dimensional (3-D) shape of the tumour by modulating or controlling the intensity of the radiation beam in such a way to focus, as much as possible, the higher radiation dose to the tumour while minimizing radiation exposure to healthy surrounding tissues. IMRT usually uses a multi-leaf collimator (MLC) that can vary the radiation beam intensity across the target. Therefore, the healthy surrounding tissue receives a smaller dose of radiation than the tumour does. The dose modulation can be used to achieve a higher dose in the tumour, a better homogeneity in the target volume or even a desired inhomogeneity to account for radiation sensitivity of different tumour areas. Treatment is carefully planned using 3-D computed tomography (CT) images of the patient in conjunction with computerized dose calculations to find out the beam cross section intensity pattern that will best conform the dose to the tumour shape. Typically, combinations of several intensity-modulated fields coming from different beam directions produce a custom tailored radiation dose that maximizes tumour dose while also protecting adjacent normal tissues. With the IMRT approach, higher and more efficient radiation doses can safely be delivered to tumours with fewer side effects compared with conventional radiotherapy techniques. IMRT also has the potential to reduce treatment toxicity, even when doses are not increased.

Treatment planning for IMRT is obviously more complex than for conventional radiation therapy, extending the treatment planning time required for each patient. The complexity of the treatment delivery makes it difficult for the operators to detect, during the delivery, possible deviations from the planned sequence of irradiations, contrary to the conventional delivery.

Before planning a treatment, a physical examination and medical history review is performed. Further, a treatment simulation session is also performed, which includes CT scanning, from which the radiation oncologist specifies the three-dimensional shape of the tumour and normal tissues. The dosimetrist and medical radiation physicist use this information to choose the treatment plan. Several additional scanning procedures, including positron emission tomography (PET) and magnetic resonance imaging (MRI), might also be required for IMRT planning. These diagnostic images help the radiation oncologist to determine the precise location of the tumour target. Typically, IMRT sessions begin about a week after simulation. Typically, patients are scheduled for IMRT sessions five days a week for six to ten weeks.

The efficacy of radiation therapy relies on the accuracy of dose delivery, and, as a result, quality assurance procedures used to detect dosimetric errors are of critical importance. Examples of such procedures are measurements in order to verify the accuracy of the delivery of the planned doses calculated by treatment planning systems, and the acquisition of orthogonal portal images to ensure accurate patient positioning with respect to the treatment machine isocenter.

IMRT places even more stringent demands on these verification procedures, and makes them even more essential. The high dose gradients in IMRT fields make single point-dose measurements inadequate for verifying the significantly non uniform dose distributions. Errors in the individual IMRT beam dose distributions calculated by treatment planning systems can occur because interleaf leakage of the multi-leaf collimator (MLC) is, for example, not accurately accounted for. The potential for systematic errors in the transfer of MLC leaf sequence files from the treatment planning computer to the record and verify system, and in the mechanical accuracy of the MLC leaf movements during beam delivery further necessitates the use of accurate IMRT verification strategies.

IMRT further requires a detailed database of the measured photon fluences delivered to the patients. Such measurements are necessary to the radiation oncologist in order to perform analysis on the biological prediction of tumour control probability and normal tissue complication probability, i.e. on the effectiveness of the protocols.

All dedicated measurements must be performed before patient treatments. These preliminary tests may be performed by executing the actual treatment plan, without the patient, while recording the doses of each field with a 2-dimensional dose measurement device such as the device 'MatriXX' manufactured by the applicant located at or near the isocenter. These measurements, however, can detect only delivery errors in the single fields and cannot be used for computing the resulting 3-dimensional dose to the patient. Moreover, such measurements cannot detect stochastic delivery errors and will not show a malfunction occurring during the subsequent patient treatment.

Further, all film-based prior art procedures are too cumbersome for day-to-day routine, and normally fluence-based verifications take the same amount of time as the treatment. This verification is therefore executed once for every plan rather than for every fraction. Fraction-to-fraction variations cannot be detected in this way. Intensified machine QA alone can be considered as being too weak for assuring perfect quality of the treatment and calculation procedures rely only on theoretical leaf sequence values, or on leaf position values determined by the system to be checked. Thus, this can be considered (at least partially) as a tautological approach. Malfunctions of the MLC are often of stochastic character rather than systematic errors.

It is known from document U.S. Pat. No. 6,038,284 a system and a method for radiation therapy delivery. This system comprises a measurement chamber 60 which is located between an accelerator and a beam shielding device 401 and which measures the integral output (monitor units) of the radiation beam exiting said accelerator. According to this method, the measurement chamber 60 directly controls the accelerator by instructing a control unit to turn the beam on and off (steps 520, 522 and 524 of FIG. 5). It is evident that this system does not provide any monitoring of the delivery, since it directly and automatically modifies the delivery system without showing possible errors to an operator. Furthermore, since said measurement chamber 60 is located between the accelerator and the beam shielding device 401, this system is not capable of detecting and signalling malfunctions of the beam shielding device 401. As a consequence, this system is not capable of providing an independent and complete monitoring of the delivery of said radiation beam which takes in account also errors due to malfunctions of the MLC.

Therefore, there is a need for a method and a device for monitoring and/or signalling errors of the delivery of a radiation treatment which does not interfere with the delivery. More particularly, there is a need for a device and method capable of providing a monitoring of the delivery whereby it is possible to detect and communicate to an operator all possible errors and let in real time the operator freely take all relevant decisions about the delivery.

A known system which is suitable for permanent in vivo verification of IMRT is provided by B. Poppe and al., "DAVID-a translucent multi-wire transmission ionization chamber for in vivo verification of IMRT and conformal irradiation techniques", Phys. Med. Biol. 51 (2006) 1237-1248. This system performs quality assurance measurement while the patient is treated. In this system a flat, translucent multi-wire ionization chamber is located in the second accessory holder of the accelerator, on the radiation entrance side of the patient. Each detection wire is located exactly in the projection line of a MLC leaf pair, and the signal of each wire is proportional to the line integral of the ionization density along this wire. After the dosimetric verification of an IMRT plan, the values measured by this system are used as reference values and stored, in order to be compared to signals that are measured during daily treatment. As a consequence, if a malfunction occurs during the measurements of those signals that will be stored as reference values all subsequent comparisons will not use correct reference values. The strongest limitation of such a system, however, is that it provides only measurements of the line integral and therefore provides only measurements of the opening of an MLC leaf pair rather than the positions of the single leaves. Therefore a possible leaf displacement where both leaves of a leaf pair are erroneously shifted to the same displacement and in the same direction cannot be detected. Another limitation of this system is that it only verifies the correct delivery of a given plan, but not possible errors arising from poor modelling inside the treatment planning system or from wrong input parameters to the treatment planning system (TPS). This limitation might give a relevant mismatch between the delivered and the calculated dose distributions. A typical example of such an error could be a poor modelling of the collimator interleaf leakage radiation which might result in a high contribution of the leakage radiation in fields with a large number of segments. Such a mismatch between the calculated and the delivered plan would not be detected by the 'David' system. Additionally, the design of this device with an air-filled active volume common to all collecting wires gives an intrinsic limitation in the detection capability of a leaf position error due to the scattering signal given by the laterally scattered secondary electrons. Moreover, the acquisition speed of one second makes this device only suitable for the step and shoots IMRT delivery technique, as in dynamic IMRT the leaf speed can be as high as some cm/s and therefore during the acquisition cycle of one second a position error of more than 1 cm could arise. Finally, another limitation of this device is that it does not provide automatic correction of air density and therefore a 40×40 field needs to be measured each morning.

Current systems are not arranged for detecting this kind of delivery error.

Aims of the Invention

The present invention aims to provide an IMRT verification device that overcomes the limitations and drawbacks of the state of the art.

Furthermore, another aim of the present invention is to provide a device and method for signalling errors of the machine delivery, and therefore, a device and method which provide surveillance of the delivery of a radiation treatment.

SUMMARY OF THE INVENTION

According with a first aspect of the invention, it is provided a method for monitoring and/or signalling errors of a radiation therapy apparatus during delivery of a radiation treatment to a target, said radiation therapy apparatus being configurable for a given radiation treatment by means of a beam shaping device, such as a multileaf collimator, the method comprising the steps of:
  providing a radiation transparent (2D) array detector between said beam shaping device and said target, capable of providing a measured (2D) detector response of said radiation treatment;
  determining a predicted (2D) detector response for successive times of said radiation treatment;
  measuring said measured (2D) detector response caused by the radiation beams for corresponding successive times of said radiation treatment;
  performing a comparison between the measured detector response and the corresponding predicted detector response;
  signalling in a short reaction time, an error when said comparison results in a difference which exceeds a given threshold.

Advantageously, according with the first aspect of the invention, said step of determining the predicted detector response of said radiation treatment further comprises the steps of:
  using a beam model of said radiation therapy apparatus, said beam model based on a set of machine parameters and on a set of beam model parameters;
  providing a set of machine parameters by importing a treatment plan from a treatment planning system;
  providing a set of beam model parameters for said radiation therapy apparatus;
  obtaining an expected fluence, by means of a fluence algorithm, said set of beam model parameters, said beam model, and said set of machine parameters imported by said treatment plan;
  obtaining the predicted (2D) detector response by means of said fluence, a detector model and a response calculation algorithm.

According with the first aspect of the present invention, in another embodiment of this method, the step of determining the predicted detector response of said radiation treatment is performed by means of a Monte Carlo simulation technique.

According with the first aspect of the present invention, in another embodiment of the method, said step of determining the predicted detector response of said radiation treatment is performed by measurements of the radiation beam of said treatment plan before the actual delivery of said radiation treatment.

More advantageously, according with the first aspect of the invention, the method further comprises the step of suggesting modifications to the treatment plan.

According with a second aspect of the invention, it is provided a device for monitoring and/or signalling errors of a radiation therapy apparatus during delivery of a radiation treatment to a target, said radiation therapy apparatus being configurable for a given radiation treatment and comprising a radiation source and a beam shaping device, the device comprising:
  detecting means located between said beam shaping device and said target, capable of providing for successive times of said radiation treatment a detector response of said radiation treatment;
  processing means comprising:
    means for acquiring in real time the measured detector response for successive times of said radiation treatment delivery;
    a memory for storing the predicted detector response for corresponding successive times of said radiation treatment;
    computing means for comparing the measured detector response and the corresponding predicted detector response in real time;
    means for signalling, in real time, an error when said comparison results in a difference which exceeds a given threshold.

Advantageously, according with the second aspect of the invention, said processing means comprises:
  means for acquiring in real time the measured detector response for successive times of said radiation treatment delivery before the actual delivery of said radiation treatment to a target;
  means for storing said measured detector response in said memory for storing the predicted (2D) detector response for corresponding successive times of said radiation treatment;

More advantageously, according with the second aspect of the invention, said processing means further comprises means for suggesting modifications to the treatment plan.

More preferably, according with the second aspect of the invention, said detector is an electronic transmission detection system with a linear response to dose and resolving in space and time.

More advantageously, according with the second aspect of the invention, this device is adapted for cooperating with an existing radiation therapy apparatus.

DETAILED DESCRIPTION OF PREFERRED EMBODIMENTS OF THE PRESENT INVENTION

Figure 1:
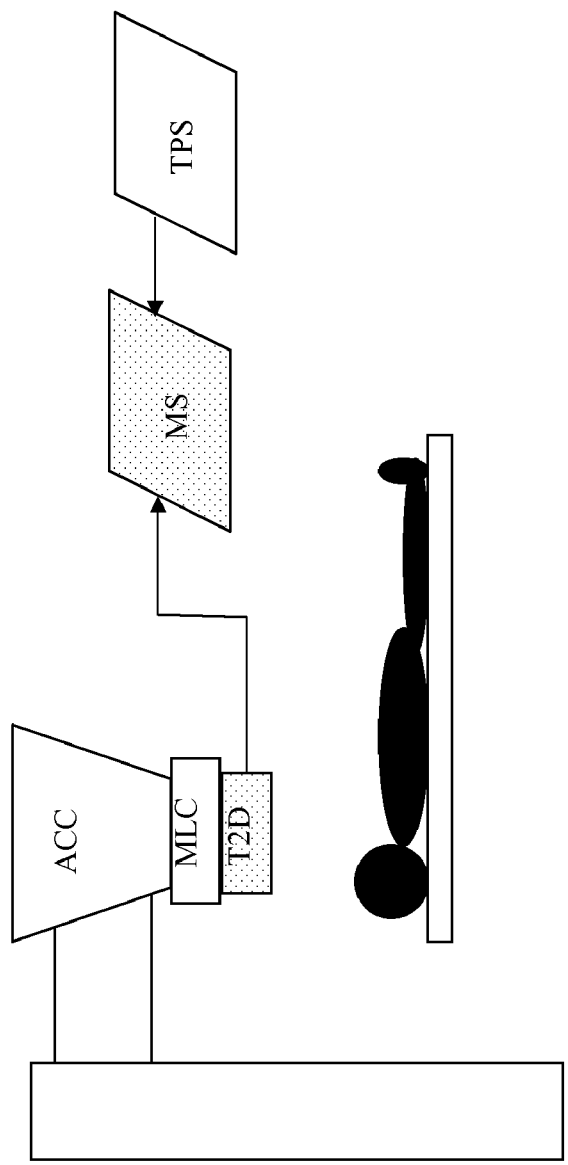
FIG. 1 shows a schematic view of a device, according to the invention.

The present invention is intended to be used with a IMRT apparatus, which delivers high energy x-ray beams from an isocentric gantry linear accelerator, and especially with an IMRT apparatus wherein the beam modulation is accomplished by means of a beam shaping device, such as a multi leaf collimator (MLC), jaws or a specific aperture.

According to a preferred embodiment, the present invention relates to a method for providing a surveillance of the delivery of a radiation treatment by a radiation therapy apparatus to a patient, said radiation therapy apparatus comprising a radiation source (ACC, MLC), the method comprising the steps of:
  providing a radiation therapy apparatus for delivery of a radiation beam, said radiation therapy apparatus being configurable for a given radiation treatment;
  providing a radiation transparent 2-D array detector (T2D) between said patient and said radiation source (ACC, MLC) capable of providing 2D detector responses (70) of said radiation beam in a plane perpendicular to the treatment beam;
  determining the predicted 2-D detector response (60) for successive times of said radiation treatment;
  delivering said radiation treatment with said radiation therapy apparatus;
  measuring the detector response (70) caused by the radiation beams for successive times of said radiation treatment;
  performing a comparison (S300) between the measured detector response (70) and the corresponding predicted detector response (60);
  signalling, in a short reaction time, an error (S400) when said comparison results in a difference which exceeds a given threshold.

Preferably, said step of determining the predicted detector response (60) of said radiation treatment further comprises the steps of:
  using a beam model (20) of said radiation therapy apparatus, said beam model (20) based on a set of machine parameters (10) and on a set of beam model parameters (30);
  providing a set of machine parameters (10) by importing a treatment plan from a treatment planning system of said radiation therapy apparatus;
  providing a set of beam model parameters (30) for said radiation therapy apparatus;
  obtaining an expected fluence (50, S100), by means of a fluence algorithm (40) of all implemented radiation qualities, a set of beam model parameters (30), said beam model (20), and said set of machine parameters (10) imported by said treatment plan;
  obtaining the predicted 2-D detector responses (60, S200) by means of said fluence (50), a detector model (400) and a response calculation algorithm (410).

Preferably, said step of determining the predicted detector response distributions of said radiation treatment is performed by means of a Monte Carlo simulation technique.

Preferably, said step of determining the predicted detector response distributions of said radiation treatment is performed by measurements of the radiation beams of said treatment plan before the delivery of said radiation treatment.

Preferably, the method of the present invention further comprises the step of suggesting modifications to the treatment plan.

According to another preferred embodiment, the present invention relates to a device for radiation therapy apparatus verification, comprising:
  a radiation transparent 2-D array detector (T2D);
  a main software (MS);

characterized in that said detector (T2D) and said main software (MS) are arranged to perform said method.

Preferably, said detector (T2D) is an electronic transmission detection system with a linear response to dose and resolving in space and time.

Preferably, said detector (T2D) is placed between said patient and said radiation source (ACC, MLC).

According to another preferred embodiment described in FIG. 1, the present invention is intended to be used additionally with common IMRT components such as a linear accelerator (ACC), MLC, accelerator control system, leaf sequencer and a treatment planning system (TPS). Other conventional components such as electronic portal imaging device (EPID), diagnostic computed tomography, real-time imaging system, etc. . . . may be added in order to perform additional features according to the present invention. The present invention comprises:

2-dimensional radiation transparent detector T2D located between the beam shaping device (MLC) and a patient or target;

a main software MS;

which are represented by the point filled blocks.

In particular, according to this preferred embodiment of the present invention, said processing means MS comprises:

means for acquiring in real time a measured detector response 70 for successive times of said radiation treatment delivery (such an acquisition means may be for example the recycling integrator developed as a 0.8 μm CMOS technology chip (TERA06) by INFN (Istituto Nazionale di Fisica Nucleare, Torino);

a memory for storing a predicted 2-D detector response 60 for corresponding successive times of said radiation treatment;

computing means for comparing S300 said measured detector response 70 and said corresponding predicted detector response 60 in real time;

means for signalling, in real time, an error S400 when said comparison results in a difference which exceeds a given threshold.

The device of the invention may be added to any existing radiation therapy apparatus, as an add-on, without interfering with the operation mode of the radiation therapy apparatus. The 2D transmission detector T2D may be easily inserted into exiting radiation apparatus by means of a special adaptor. This adaptor takes place into rails which are typically provided for installing special equipment into a radiation apparatus. The main software MS runs on a stand-alone computer which is may be monitored by an operator and is connected to the accelerator in order to acquire information (in a convenient format, such as DICOM format) on the delivery.

The 2-dimensional radiation transparent detector T2D is used to provide a 2-dimensional map of measurements on a plane orthogonal to the beam direction, but without causing a relevant perturbation of the therapeutic beam which invest a patient after having crossed such a detector. Therefore, a radiation transparent 2-D array detector T2D, suitable for the present invention, allows a beam transmission of 95% or more and does not induce a beam modulation of more than 2%. A technology used to realize such a T2D for hadron beams is described by Bonin and al. in "A pixel chamber to monitor the beam performances in hadron therapy", Nuclear Instruments and Methods in Physics research, A 519 (2004)- 674-686. This document describes a device made up of a 2-D array of 1024 ionisation chambers arranged in a regular matrix of 32×32 pixels. This technology is also used in the commercial product MatriXX manufactured by the Applicant which has been modified for usage with photon beams by providing additional material in the air volume to provide lateral electronic equilibrium for each chamber of the detector. By using this technology, a fast simultaneous read out of all chambers is possible. The read out speed per channel is 200 ns. A full read out cycle (1024 pixels) takes 500 μs, of which ≈300 μs are due to the overhead of the start-up phase. However, this detector is not optimized for providing maximum transmission, as it is part of a sandwich-like structure including backscatter and build-up materials and is intended to be used for dose measurements at isocenter. The total thickness of this kind of device was therefore not kept as small as possible. In order to obtain the radiation transparent 2-D array detector T2D, suitable for the invention, the total thickness was further reduced. According to the present invention, the transmission detector T2D is made up of an array or matrix of pixel ion chambers. Each pixel ion chamber has a top electrode, a mid layer, and a segmented electrode. The top electrode has a polyimide layer sandwiched on both sides by two carbon layers. The top electrode could be made from any material, depending on the application such as, for example another plastic material, graphite, or metal. Preferably the polyimide is about 50 μm thick. Preferably the carbon layers are printed carbon of about 25 μm thick. The inner carbon layer is structured according to hole of the mid layer and dimensioned so that the circumference of the inner carbon layer fits into and is smaller than the circumference of the hole. The inner carbon layer is about 4.4 mm diameter, and the corresponding hole in mid layer has a diameter of about 4.5 mm. Further the mid layer is constructed of pure polycarbonate plate and is about 5 mm thick, but can larger or smaller depending on the diameter of the chamber. In the approximate center of said mid layer, a hole extends through the entire thickness of the mid layer. The hole is preferably about 4.5 mm in diameter and extends substantially perpendicular to the horizontal plane of mid layer to form a cylinder. The top end of mid layer is laminated to the polyimide layer of top electrode by means of an adhesive. Preferably the adhesive is in the form of adhesive dots that are about 100 μm thick. The adhesive material is preferably epoxy with a diameter from about 1 to 2 mm. The bottom end of mid layer is likewise laminated to the top layer of the segmented electrode by an adhesive, which is preferably in the form of adhesive dots. Once the mid layer is adhered to the top and segmented electrode, chamber is formed in the hole of the mid layer. Another important feature of the transmission detector T2D is that it is able to continuously monitor the photon fluence modulated by the movements of the multi leaf collimator. Therefore a geometrical correspondence between the pitch of the 2D array of detector pixels and the leaf width of the MLC is realized. This is achieved, for example, when the pixel pitch projection at isocenter is the same as the projected leaves width, or if it is an integer fraction of it.

Figure 2:
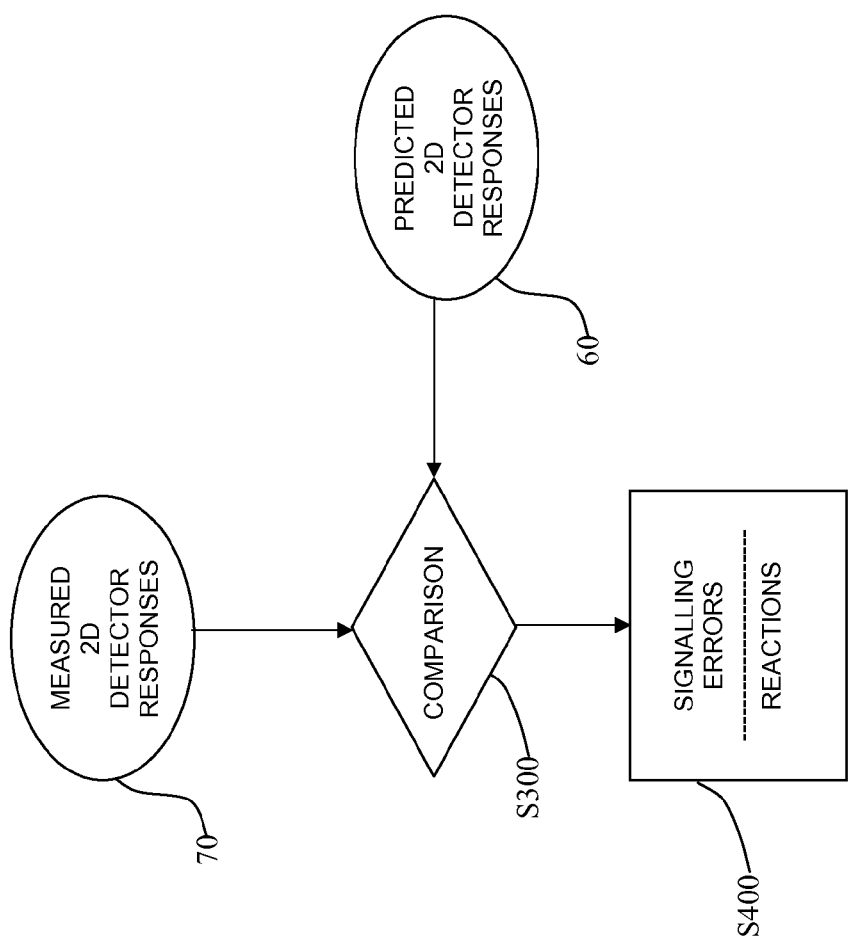
FIG. 2 is a dataflow diagram which represents a method according to the invention.

We refer now to FIG. 2. According to the present invention, firstly a sequence of successive expected detector responses 60 is calculated. Next, beam measurements are performed by setting the application into measurement mode. In the present invention, a 2-dimensional transmission detector T2D is provided upstream of the patient, between said patient and the head of the accelerator. During the radiation treatment delivery, successive 2-D detector responses 70 are acquired with an interval of 10 ms. Each measurement is stored and processed online. Before the next measurement is stored, as shown in S300, a comparison of the measured detector response 70 with the corresponding predicted detector response 60 is performed, and such a comparison will be based on a sequence derived from the comparison of the integral of the expected to the integral of the measured response of all detector pixels. When using the step-and-shoots delivery method, this comparison can be performed between successive shoots. By contrast, when using the dynamic IMRT delivery method, this comparison can be performed periodically or at control points and therefore it is possible to signal errors in a short reaction time, as shown in S400.

A beam model is a mathematical description of a radiation therapy apparatus in general, which contains a number of parameters. These parameters take into account e.g. the characteristics of the accelerator (energy spectrum, lateral beam quality variations), the shapes and positions of the effective radiation sources, and the geometry and material of the beam shaping devices. A fluence computation algorithm is a set of mathematical rules which allows computing the fluence according to the beam model and a given parameter set. The representation of the computed fluence (units, coordinate systems) is such that it is compatible with additional computational procedures for computing detector response and/or deposited dose. Useful descriptions of basic beam modelling techniques are provided, for example, by Wolfgang A. Tomé, "Beam Modelling for a Convolution/Superposition-Based Treatment Planning System", Medical Dosimetry, Vol. 27, No. 1, pp. 11-19, 2002; or by Nikos Papanikolaou, "Investigation of the convolution method for polyenergetic spectra", Med. Phys. 20(5), 1993.

For a given application, a beam model for the treatment machine is selected. Also an initial machine parameters set sequence is chosen according to the settings of the treatment machine (beam quality and dose, dose rate, MLC position) and a 2D detector transmission system, the latter being capable of measuring a 2-D response of the applied fields.

Figure 3:
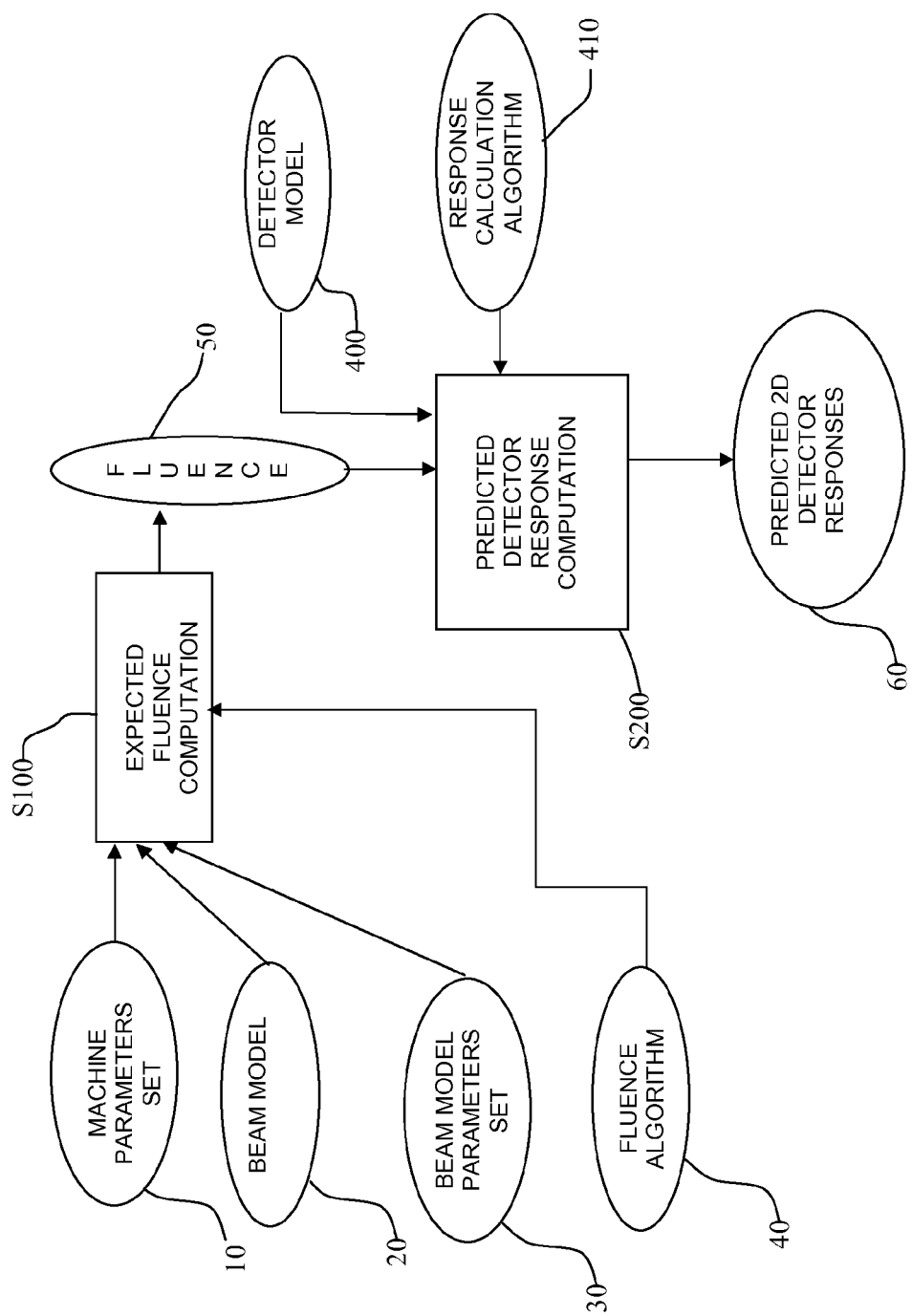
FIG. 3 is a dataflow diagram which represents a method for predicting 2-D detector responses for use in the present invention.

According to a preferred embodiment of the present invention, a method for determining the predicted 2D detector response 60 is hereafter described. By referring to FIG. 3, a set of machine parameters 10 is provided by importing a treatment plan from a treatment planning system, and is then directed to the dose/fluence engine, wherein one computes the expected fluence 50 by means of a beam model 20, a set of beam model parameters 30 corresponding to said radiation apparatus, and by means of a fluence algorithm 40, as shown in step S100. As shown in step S200, said expected fluence 50 is used to compute the predicted detector responses 60 using a detector model 400 describing the geometry of the device and a response calculation algorithm 410 describing the device response to irradiation in a resolution determined by a given number of MUs (Monitor Units)—e.g. 1 MU. For segmented delivery, this is the response for the segment divided by the number of monitor units for this segment. For dynamic delivery, the position of leaf $P_m(\phi)$ between the positions of the leaf at the control points $P_m^i$ and $P_m^j$ is given by the following equation:

$$P_m(\varphi) = P_m^i + \frac{\varphi - \varphi_i}{\varphi_j - \varphi_i}(P_m^j - P_m^i);$$

where $\phi$ is the detector response.

For each measured frame, the integral of the responses of all pixels will be compared to the predicted integral. If the measured integral is equal or larger than the predicted one, a precise comparison of the shape of the measured and predicted responses can be performed. In fact, when measurements are not synchronized with the predictions then for a given measurement one can obtain the corresponding prediction only before and after that measurement. Therefore, in order to obtain said prediction one has to interpolate, between two predictions corresponding to two control points with the same number of elapsed MUs.

Once the predicted 2-D detector responses are obtained, the precise comparison of the shape of the measured and predicted responses can be performed and fail/pass criteria can be applied. The tolerance of the fail/pass criteria is a function of a user definable percentage with regards to an average over a definable number of pixels. If the difference between the integral of the predicted response and the integral of the measured response on at least the selected number of random pixels is above the tolerance at the current number of elapsed MUs, a warning will be issued in order to signal errors and, if necessary, perform modifications, as shown in S400 of FIG. 2.

Said detector response can also be determined, according to other embodiments of the present invention, by using, for example, the Monte Carlo simulation technique, or by performing measurements off-line of the radiation treatment.

Figure 4:
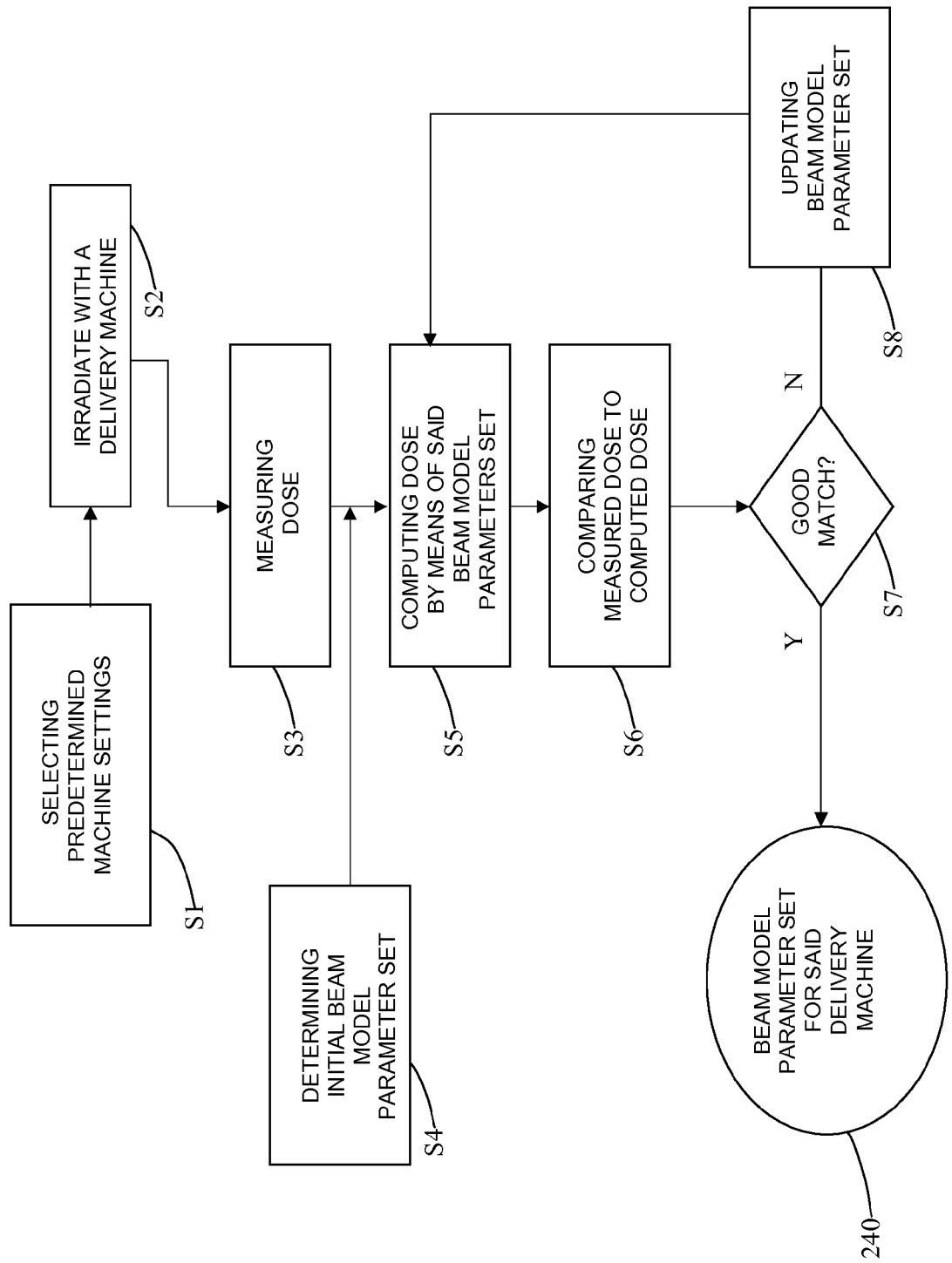
FIG. 4 is a dataflow diagram which represents a method for determining a beam model parameters set, for use in the present invention.

FIG. 4 is a dataflow diagram which represents an operation performed in a variation of the invention, in order to adapt a beam model to a given delivery machine by finding a beam model parameters set that best fits the given delivery machine and T2D detector. As shown in step S1, the operator selects some predetermined machine settings. Next, as shown now in step S2 and S3, the delivery machine to be modelled is used to irradiate a phantom using the said machine settings, and, by using detector means, the dose is measured. In step S4, a beam model parameter set for a similar delivery machine is selected, and using this, the dose is computed in step S5 in the same points as the measurements. The computed and measured doses are compared in step S6. Should the user find the match adequate, in test S7, the current beam model parameter set is said to represent the delivery machine in step 240. Otherwise, the beam model parameter set is modified, manually or automatically, as shown in step S8 and a dose computation is carried out, returning to step S5.

By using the present invention one can perform an online monitoring and verification of the delivery of the patient fields by accessing the expected photon fluences from the TPS and comparing them to the delivered photon fluences through the expected and measured detector responses. The monitoring and errors signalling provided by the invention allow an operator to detect unexpected malfunctions of the radiation therapy apparatus. In case of an error the operator may interrupt the treatment, so as, from the data acquired, the therapist may then adapt the treatment for subsequent fractions. The apparatus of the invention therefore improves the security of the delivery of the treatment but does not interfere with the treatment applied.

Finally, another advantage achieved by using the present invention is to provide an IMRT verification system which reduces global costs and time required by avoiding the cumbersome and long lastiorg state-of-art verification and QA procedures for IMRT

The invention claimed is:

1. A method for monitoring and/or signaling errors of a radiation therapy apparatus during delivery of a radiation treatment to a target, the radiation therapy apparatus being configurable for a given radiation treatment by a beam shaping device, the method comprising:
   providing a radiation transparent array detector between the beam shaping device and the target, the radiation transparent array detector being configured to provide a measured detector response of the radiation treatment;
   determining a predicted detector response for successive times of the radiation treatment;

measuring the measured detector response for corresponding successive times of the radiation treatment;

performing a comparison between the measured detector response and the corresponding predicted detector response; and signaling in a short reaction time, an error when the comparison results in a difference which exceeds a given threshold.

2. The method according to claim 1, wherein determining the predicted detector response of the radiation treatment further comprises:

using a beam model of the radiation therapy apparatus, the beam model based on a set of machine parameters and on a set of beam model parameters;

providing a set of machine parameters by importing a treatment plan from a treatment planning system;

providing a set of beam model parameters for the radiation therapy apparatus;

obtaining an expected fluence, by a fluence algorithm, the set of beam model parameters, the beam model, and the set of machine parameters imported by the treatment plan; and obtaining the predicted detector response by the fluence, a detector model and a response calculation algorithm.

3. The method according to claim 1, wherein determining the predicted detector response of the radiation treatment is performed with a Monte Carlo simulation technique.

4. The method according to claim 1, wherein determining the predicted detector response of the radiation treatment is performed by measurements of the radiation beam of the treatment plan before the delivery of the radiation treatment.

5. The method according to claim 1, wherein the method further comprises suggesting modifications to the treatment plan.

6. A device for monitoring and/or signaling errors of a radiation therapy apparatus during delivery of a radiation treatment to a target, the radiation therapy apparatus being configurable for a given radiation treatment and comprising a radiation source and a beam shaping device, the device comprising:

a detector located between the beam shaping device and the target, the detector being configured to provide for successive times of the radiation treatment a measured detector response of the radiation treatment; and a processor device comprising:

an acquisition device configured to acquire in real time the measured detector response for successive times of the radiation treatment;

a memory configured to store a predicted detector response for corresponding successive times of the radiation treatment;

a comparison device configured to compare the measured detector response and the corresponding predicted detector response in real time; and a signal device configured to signal in real time, an error when the comparison results in a different which exceeds a given threshold.

7. The device for monitoring and/or signaling errors according to claim 6, wherein the processor further comprises a determinator device configured to determine a predicted 2-D detector response for corresponding successive times of the radiation treatment.

8. The device for monitoring and/or signaling errors according to claim 6, wherein the processor device further comprises:

an acquisition device configured to acquire in real time the measured detector response for successive times of the radiation treatment delivery before the actual delivery of the radiation treatment to a target; and a storage device configured to store the measured detector response in the memory for storing the predicted detector response for corresponding successive times of the radiation treatment.

9. The device for monitoring and/or signaling errors according to claim 6, wherein the processor device further comprises a modification device configured to suggest modifications to the treatment plan.

10. The device for monitoring and/or signaling errors according to claim 6, wherein the detector is an electronic transmission detection system with a linear response to dose and resolving in space and time.

11. The device for monitoring and/or signaling errors according to claim 6, wherein the device is configured to cooperate with an existing radiation therapy apparatus.

12. The device for monitoring and/or signaling errors according to claim 6, wherein the device is configured to operate independently from the radiation therapy apparatus.

* * * * *